United States Patent
Van Dijk et al.

[11] 3,937,841
[45] Feb. 10, 1976

[54] TREATMENT OF DEPRESSION

[75] Inventors: Jan Van Dijk; Jenkins Eric Davies, both of Weesp, Netherlands

[73] Assignee: U.S. Philips Corporation, New York, N.Y.

[22] Filed: Oct. 24, 1974

[21] Appl. No.: 517,519

Related U.S. Application Data
[62] Division of Ser. No. 279,971, Aug. 11, 1972.

[52] U.S. Cl. .............. 424/327; 424/246; 424/263; 424/276; 424/282
[51] Int. Cl.² .............. A61K 31/15; A61K 31/36; A61K 31/39; A61K 31/44; A61K 31/54
[58] Field of Search ................ 260/566 AE, 465 E; 424/327

[56] References Cited
UNITED STATES PATENTS
3,429,919  2/1969  Koopman .......................... 260/564

Primary Examiner—Stanley J. Friedman
Attorney, Agent, or Firm—Frank R. Trifari; Norman N. Spain

[57] ABSTRACT

The invention relates to new compounds of formula I

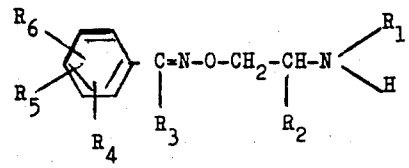

and salts thereof with pharmaceutically acceptable acids, in which formula all the substituents may be hydrogen, while $R_1$ and $R_2$ may furthermore be a methyl group, $R_3$ an alkyl group, an alkoxy-alkylene group, an alkylthioalkylene group, an alkylsulphoxyalkylene group or an alkylsulphonalkylene group having up to 8 carbon atoms or a benzyl group, and $R_4$, $R_5$ and $R_6$ a halogen atom, an alkyl group, an alkoxy group or an alkylthio group having up to 6 carbon atoms, a benzyloxy group, —OH, —$NH_2$, a mono- or dialkylamino group, in which the alkyl group(s) contain(s) 1 or 2 carbon atoms, —CN or —$CF_3$, and two of the substituents $R_4$, $R_5$ and $R_6$ may each represent a metanitro group or together a trimethylene group, a tetramethylene group, a methylene dioxy group, an ethylene dioxy group, a benzo group, a pyridino group, an indeno-1,2-, a 1,4-benzthiazino-2,3 group or a 1,4-benzoxthiino-2,3 group, with the exception of the HCl salt of the compound in which $R_5$ and $R_6$ each represent an orthochlorine atom and $R_1$, $R_2$, $R_3$ and $R_4$ each represent hydrogen.

4 Claims, No Drawings

TREATMENT OF DEPRESSION

This is a division of application Ser. No. 279,971, filed Aug. 11, 1972, and now abandoned, said application Ser. No. 279,971 being a division of application Ser. No. 715,571, filed Mar. 25, 1968 and now United States Patent 3,692,835.

The compounds according to the invention have interesting pharmacological properties. They have in particular a very strong central activity which may be expressed both in an anti-depressive activity, whether or not caused by monoamino oxidase inhibition, and in a sedative or anticonvulsive activity.

In particular those compounds according to the invention in which both $R_1$ and $R_2$ represent a hydrogen atom have a strong activity.

The monoamino oxidase inhibiting effect of compounds of formula I was found in experiments in which a quantity of the compound to be tested was administered intraperitoneally or orally to five male albino mice. One hour after the administration the animals were injected subcutaneously with tryptamine hydrochloride in a quantity of 250 mgms/kgm. This quantity caused no mortality in animals which had not received the compound to be tested but dis cause mortality in the animals which had been treated. Eighteen hours after the administration of tryptamine hydrchloride it was determined how many treated animals had died. The $ED_{50}$ was determined from the results.

The antidepressive effect of compounds of formula I was also determined in the tetrabenazine test. In this test a quantity of the compound to be tested was administered intraperitoneally or orally to five male albino mice. After 45 minutes the animals were injected subcutaneously with 80 mgms per kgm of tetrabenazine. After another 45 minutes the degree of ptosis was determined and compared with the ptosis of animals which had received tetrabenazine alone. The $ED_{50}$ was determined from the results.

The sedative effect of compounds according to the invention was found in the hexobarbital narcotising test. In this test a compound to be tested was administered intraperitoneally and orally, respectively, 60 minutes prior to a dose of hexobarbital (30 mgms/kgm) which was just less than narcotic. Induction of narcosis was the criterion for the activity of the substance. The $ED_{50}$ was calculated from a series of experiments with varying dosages.

The anticonvulsive effect of compounds according to the invention against superamaximal electric shock was determined in female mice 30 minutes after an intraperitoneal administration or 60 minutes after an oral administration of the compound to be tested.

The influence of compounds on the convulsive effect of a supramaximal intravenously administered dose of pentamethylene tetrazol (50 mgms/kgm) was also determined in female mice 30 minutes after an intraperitoneal administration or 60 minutes after an oral administration of a compound.

The antidepressive compounds according to the invention are particularly suitable for use in the therapy of neurotic and psychotic disturbances, in particular of the depressive syndrome and also for the treatment of psychosomatic disturbances. The substances may therefore be administered to depressive patients as a psychostimulant.

The sedative compounds are excellently suitable for use as an ataractic. They may successfully be used for the treatment of mild psychoneurotic phenomena.

The anti-convulsive compounds may be used in the treatment of epileptic patients.

The cmpounds, including the HCl salt of O-(2-amino-ethyl) 2,6-dichlorobenzaldoxim, may be administered in the conventional manners after having been brought in a suitable form of administration. They may be injected or be administered orally or rectally. As forms of administration are therefore to be considered inter alia: injection liquids, pills, tablets, coated tablets, capsules, powders, and the like.

The way in which, the quantity in which and the frequency with which the substances are to be administered to the patient may vary for each individual patient also in accordance with the severity of the disturbances. In general, the practitioner will have no trouble in choosing the correct therapy for a given patient.

The dosing of sedative and antidepressive compounds will in general be from 10 to 500 mgms daily for adults. As a rule a quantity of from 10 to 150 mgms will be sufficient.

Anti-convulsives according to the invention will generally be administered in dosages of from 100 to 500 mgms daily.

The compounds according to the invention, including the HCl salt of 0-(2-aminoethyl)2,6-dichlorobenzaldoxim may be processed according to methods commonly used in pharmacy to compositions, for example, by mixing an active substance with or dissolving it in solid or liquid carriers.

As such are to be considered the conventional carriers, for example, water made isotonic with blood, if desired, for example, by means of kitchen salt, glycerin, chalk, calcium phosphate, lactose, powdered sugar, calcium carbonate. As swelling agents in tablets and coated tablets may be used, for example, potato starch, maize starch, arrow root (amylum marantae), carboxy methylcellulose, gelatin and acacia gum.

As lubricants may be used talcum, magnesium stearate, calcium stearate, and stearic acid. Compositions for oral administration may contain in addition flavouring substances, for example, sugars or vanilla extract.

As preservatives may be used, for example, propyl-p-hydroxy-benzoate and benzyl alcohol. The compositions may contain in addition surface-active substances, for example, mono-, di- and tri-esters of higher fatty acids.

As examples of pharmaceutically acceptable acids with which the compounds can form salts may be mentioned: hydrohalogenic acids, for example, hydrochloric acid, hydrobromic acid, in addition other inorganic acids, for example, sulphuric acid, nitric acid, phosphoric acid, and organic acids, for example, citric acid, acetic acid, oxalic acid, fumaric acid, lactic acid, succinic acid, sulphamic acid, benzoic acid, tartaric acid, and gallic acid.

The compounds according to the invention may be prepared according to methods which are known per se.

The invention therefore also relates to a method of preparing new oxim ethers, characterized in that compounds of formula I

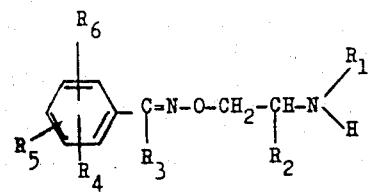

and salts thereof with pharmaceutically acceptable acids, in which formula all the substituents may be hydrogen while $R_1$ and $R_2$ may furthermore represent a methyl group, $R_3$ an alkyl group, an alkoxyalkylene group, an alkylthioalkylene group, an alkylsulphoxyalkylene group, an alkylsulphonalkylene group having up to 8 carbon atoms or a benzyl group, and $R_4$, $R_5$ and $R_6$ may each be a halogen atom, an alkyl group, an alkoxy group or an alkylthio group having up to 6 carbon atoms, a benzyloxy group, a hydroxy group, an amino group, an alkylamino group or a dialkylamino group, in which the akyl group(s) contain(s) 1 or 2 carbon atoms, a nitrile group or a trifluoromethyl group and two of the substituents $R_4$, $R_5$ and $R_6$ may each be a meta nitro group or together a trimethylene group, a tetramethylene group, a methylenedioxy group, an ethylenedioxy group, a benzo group, a pyridino group, an indeno-1,2 group, a 1,4-benzthiazino-2,3 group or a 1,4-benzoxthiino-2,3 group, with the exception of the HCl salt of the compound in which $R_5$ and $R_6$ each represent an orthochlorine atom and $R_1$, $R_2$, $R_3$ and $R_4$ each represent a hydrogen atom, are prepared according to methods which are known for the preparation of this type of compounds and according to methods analogous thereto.

For example, compounds according to the invention may be prepared by reacting a compound of formula II

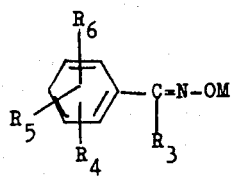

wherein M is a hydrogen atom or an alkali metal atom, with a compound of formula III

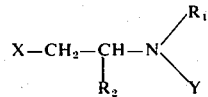

wherein X is a halogen atom, preferably a bromine or chlorine atom or a tosyloxy group and Y is a hydrogen atom or an acyl group, for example, an alkoxycarbonyl group or a carbobenzoxy group, which, after the coupling reaction, is split off by hydrolysis.

The reaction may be carried out in a suitable solvent. As such are to be considered inter alia: alcohols, for example, methanol, ethanol, ketones, for example, acetone and methylethyl ketone, and ethers, for example, dioxane and dimethylglycol ether.

When M in formula II is a hydrogen atom, it may be recommendable to add an acid binder to the reaction mixture. As such may be mentioned inter alia alcoholates, potassium carbonate and sodium carbonate, tertiary amines, pyridine and the like.

The temperature of the reaction mixture may vary between rather wide limits. As a rule, however, it will be between 0° and 50°C.

The oxims of formula II may be obtained in the conventional manner from the corresponding aldehydes or ketones by means of hydroxylamine. The oximates may be prepared from the oxims by adding the oxims, whether or not dissolved in alcohol, to a solution of potassium or sodium alcoholate or -hydroxide in alcohol.

The compounds according to the invention may alternatively be obtained by reacting a compound of formula IV

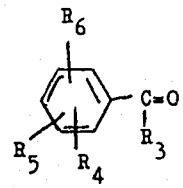

with a compound of formula V

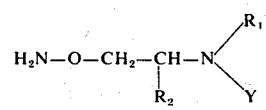

wherein Y is a hydrogen atom, or an acylgroup for example an alkoxycarbonyl group or a carbobenzoxy group which, after the coupling reaction, is split off by hydrolysis.

The reaction may be carried out in a suitable solent. As such may be mentioned: alcohols, pyridine, dioxane, dimethylformamide, tetrahydrofurane and the like or mixtures thereof. In general the reaction temperature lies between room temperature and the boiling point of the solvent. An alternative method of preparing compounds according to the invention is that in which an oxim of formula II (M = H) is reacted with an imine of the formula VI

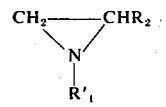

wherein $R'_1$ is an acyl group which is split off after the reaction by hydrolysis.

The reaction may be carried out in a suitable solvent, for example, dioxane, benzene.

The compounds according to the invention may also be obtained by reacting a compound of formula VII

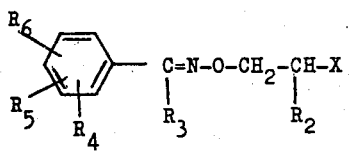

wherein X is a halogen atom, preferably a bromine atom or a tosyloxy group, with ammonia or methylamine.

The reaction may be carried out, for example, in alcohols.

The starting substances of formula VII may be obtained by reacting oxims of formula II (M = H) in the presence of an acid binder with a halogen compound of formula VIII

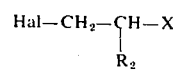

wherein X has the same meaning as in formula VII and Hal is a halogen atom, preferably a bromine atom. When in formula II one or more of the substituents $R_4$, $R_5$ and $R_6$ is a primary or secondary amino group and a hydroxy group, respectively, it is preferably protected with an acyl group and a benzyl group, respectively, which groups are subsequently split off by hydrolysis or hydrogenolysis.

In order that the invention may be readily carried into effect certain examples thereof will now be described in greater detail.

1. 4'-methyl-O-(2-aminoethyl)acetophenoneoxim-HCl

A solution of 3.23 gms of 0-(2-aminoethyl) hydroxylamine dihydrochloride and 3.35 gms of 4'-methylacetophenone in a mixture of 15 mls of pyridine and 30 mls of absolute ethanol was refluxed for 2 hours. The solvent was then distilled off in vacuo and the residue, after dissolving in little water, was washed three times with diethyl ether. 30 mls of 2N sodium hydroxide solution were then added to the washed solution and the whole was again extracted three times with ether. This ether extract was washed three times with water and then dried on sodium sulphate. After distilling off the solvent in vacuo the residue was neutralised with alcoholic hydrochloric acid. From this neutralised solution the hydrochloride of 4'-methyl-0-(2-aminoethyl)acetophenone oxim crystallised after the addition of ether. The product was crystallised again from a mixture of absolute ethanol and ether, melting point 183°– 185°C.

2. 0-(2-aminoethyl)-3',4'-ethylene-dioxy-acetophenone oxim-HCl 4.8 gms of 3', 4'-ethylenedioxyacetophenone oxim were added to a solution of 0.100 mol of sodium (2.30 gms) in 75 mls of absolute ethanol. The oxim dissolved. 0.050 mol of 2-bromoethylaminohydrobromide were then added (10.25 gms). The mixture was stirred at room temperature for 2 hours. Then it was sucked off from the NaBr formed and the filtrate was evaporated in vacuo until it was free from solvent. The residue was dissolved in water (50 mls) and ether (50 mls) and the water layer was separated. The ethereal layer was washed two times with 25 mls of water and dried on $Na_2SO_4$. The ether was removed in vacuo, an oil being formed. This oil was dissolved in approximately 20 mls of absolute alcohol and acidified with alcoholic hydrochloric acid. By the addition of ether the HCl salt crystallised out. After cooling the crystallised substance was sucked off. After crystallisation from alcohol the melting point was 203°–206°C.

3a. 0-(2-bromoethyl)4'methylhexanopheneone oxim 20.5 gms of 4'-methylhexanophenone oxim were dissolved in a solution of 4.6 gms of sodium in 100 mls of absolute ethanol. At 20°C and while stirring this solution was added to a mixture of 60 mls of 12, dibromoethane and 50 mls of N,N-dimethylformamide. The reaction mixture was then heated to 65° and kept at this temperature for 16 hours. The formed precipitate was then sucked off and the filtrate was concentrated in vacuo. After the addition of 200 mls of water the concentrate was extracted with chloroform (2 × 100 mls). The extract was dried on sodium sulphate, concentrated in vacuo and then distilled in a high vacuum (0.005 mm). The distillate (boiling point 111°–114°C/0.005 mm) contained, in addition to 4'-methyl-hexanophenone oxim, the O-(2-bromo-ethyl)-4'-methylhexanophenone oxim.

b. 0-(2-aminothyl)4'-methyl-hexanophenone oxim.HCl.

A solution of 9.0 gms of this distilled bromine compound in 50 mls of ethanol was mixed with 50 mls of concentrated ammonia. This mixture was then stirred in a closed vessel at 65° for 16 hours and then concentrated in vacuo. The concentrate was mixed with 50 mls of ether and then extracted three times with 20 mls of N hydrochloric acid. The acid extract was washed with 50 mls of ether, then rendered alkaline with 40 mls of 2N sodium hydroxide solution and again extracted three times with 30 mls of ether. This ethereal extract was dried on sodium sulphate, concentrated, and the remaining oil was distilled in a high vacuum. The distillate (boiling point 121°–122°C/0.3 mm) was taken up in 25 mls of diethylether and neutralised with 2N ethanolic hydrochloric acid as a result of which the above substance crystallised out. After crystallisation from ethyl acetate the melting point was 97°–98°C.

4a. 0-(2-p. toluene sulphoxyloxy ethyl)-4'methyl propionphenone oxim.

12.7 gms of p-toluenesulphonylchloride were added to a solution of 13.8 gms of 0-(2-hydroxyethyl)-4'-methyl propiophenone oxim (synthetised from 4' methylpropiophenone oxim and ethelene oxide under the influence of lithium ethanolate in ethanol) in 20 mls of pyridine while stirring and cooling in ice water. The reaction mixture was stirred while cooling for another 15 minutes and then at room temperature for 3 hours. The reaction mixture was then poured on a mixture of 90 gms of ice and 30 mls of concentrated hydrochloric acid. The separated solid was extracted three times with 50 mls of benzene. The solution in benzene was washed with 2N hydrochloric acid and then with dilute carbonate solution. After drying the solution on potassium carbonate the solvent was removed in vacuo and the residue crystallised from a mixture of 35 mls of benzene and 55 mls of petroleum ether.

b. 0-(2-aminoethyl)-4'-methyl propiophenone oxim HCl.

A suspension of 3.6 gms of the compound prepared sub 4a in 100 mls of concentrated ammonia and 100 mls of ethanol was shaken at room temperature for 15 hours and then at 80° for another 7 hours in an autoclave. The excessive ammonia and a part of the solvent were distilled off in vacuo until the residue turned cloudy. After the addition of 15 mls of 2N sodium hydroxide solution, this residue was extracted 3 times with totally 100 mls of ether. The ether extract was then extracted 2 times with 10 mls of 2N hydrochloric acid. This acid extract was again made alkaline with 5 mls of 50% sodium hydroxide solution and then extracted with toally 30 mls of chloroform. This extract was dried on sodium sulphate after which the solvent was removed in vacuo. The residue was distilled in a high vacuum. By neutralising the distillate with 6 mls of alcoholic hydrochloric acid and then adding 30 mls of ether, a crystalline substance was obtained. Melting point after recrystallisation from diethylether 124.5°–25.5°C.

5a. 0-{2-(N-ethoxycarbonylamino)ethyl}-4'-methyl-thioacetophenone oxim.

A solution of N-ethoxycarbonylethylene imine, obtained by reacting 1.4 mls of ethylene imine with 2.4 mls of ethylchloroformate under the influence of triethylamine in 30 mls of absolute benzene was mixed, while stirring, with a solution of 4.1 gms of 4'-methylthioacetophenone oxim in benzene. The reaction mixture was then heated to the boiling temperature while stirring and then it was stirred at this temperature for another 30 minutes. After leaving the mixture to stand at room temperature for 16 hours it was mixed with water and the benzene layer was then separated. This benzene layer was washed 3 × with water and then dried on sodium sulphate. After removing the solvent the above-mentioned substance was obtained by fractional crystallisation from ethanol and petroleum ether.

b. 0-(2-aminoethyl)-4'-methylthio acetophenone oxim.HCl

Of this ethoxy carbonyl compound 0.21 gms were dissolved in 4 mls of ethanol. After the addition of 2.0 mls of 3N sodium hydroxide solution this solution was refluxed for 4 hours. The solvent was then partly removed in vacuo and the residue extracted 3 × with ether after the addition of some water. The ethereal solution was shaken with 2.00 mls of 1.2N hydrochloric acid and, after the layers had separated, once again with water. 1.8 ml of 3N sodium hydroxide solution were added to the acid extract and the latter was extracted again two times with ether. This latter ether extract was dried on sodium sulphate, then evaporated, and the resulting residue neutralised with alcoholic hydrochloric acid after which the substance crystallised. After crystallisation from ethanol/diethyl ether 1 : 1 the melting point was 215°–219°C.

6. 0-(2-amino-ethyl)-acetophenone-oxim hydrochloride.

0.050 mol of acetophenone oxim (6.75 gms) were added to a solution of 0.200 mol of sodium (4.60 gms) in 75 mls of ethanol supra. 0.100 mol of 2-bromoethylamine hydrobromide (20.5 gms) were then added after which the mixture was stirred at room temperature for 2 hours. The formed NaBr was then sucked off and the filtrate was evaporated in vacuo until free from solvent. The residue was dissolved in 75 mls of ether +75 mls of water, the water layer was separated and the ether layer was washed two times with 25 mol of water. Subsequently the ether layer was extracted with 50 mls of 2 N HCl and then with 20 mls of water. The acid extracts were made basic with 75 mls of 2N NaOH and then extracted three times with 50 mls of ether. The collected ether extracts were washed three times with 20 mls of water and dried on $Na_2SO_4$. The ether was evaporated in vacuo as a result of which an oil was obtained. This oil was dissolved in 5 mls of absolute alcohol and acidified to pH 4 with alcoholic hydrochloric acid. A crystalline substance precipitated as a result of the addition of ether. This substance was sucked off and dried, and recrystallised from a mixture of absolute alcohol and ether. Melting point 173°–175°C.

7. 0-(2-amino-ethyl)-methyl-α-naphthyl-ketoxim-hydrochloride.

0.025 mol of methyl-α-napthyl-ketoxim (4.63 gms) were added to a solution of 0.100 mol of sodium (2.30 gms) in 75 mls of absolute ethanol. The oxim dissolved. 0.050 mol of 2-bromoethylamine hydrobromide (10.25 gms) were then added. The mixture was stirred at room temperature for 2 hours. The formed NaBr was sucked off and the filtrate was evaporated in vacuo until free from solvent. The residue was dissolved in water (50 mls) and ether (50 mls) and the water layer was separated. The ether layer was washed two times with 25 mls of water and dried on $Na_2SO_4$. The ether was removed in vacuo in which an oil was formed. This oil was dissolved in approximately 20 mls of absolute alcohol and acidified with alcoholic hydrochloric acid. By the addition of ether the HCl salt crystallised. After cooling this was sucked off. After two recrystallisations from alcohol the melting point was 236°–238°C.

8. 0-(2-amino-ethyl)-isobutyrophenone oxim hydrochloride.

0.050 mol of isobutyrophenone oxim (8.15 gms) were added to a solution of 0.200 mol of sodium (4.60 gms). This oxim dissolved substantially entirely. This was mixed with 0.100 mol of 2-bromoethyl-amine hydrobromide (20.5 gms). The mixture was stirred at room temperature for 2 hours. Then it was sucked off from the formed precipitate of NaBr and the filtrate was evaporated in vacuo until it was free from solvent. The residue was dissolved in 75 mls of ether, the water layer was extracted and the ether layer was washed 2 times with 25 mls of water. The ether layer was then acidified with 50 mls of 2N HCl, then separated and extracted once again with 25 mls of water. The acid extracts were made basic with 75 mls of 2N NaOH and extracted three times with 50 mls of ether. The collected ether extracts were washed three times with 25 mls of water and then dried on $Na_2SO_4$. After removing the ether in vacuo a colourless oil remained. This was dissolved in 10 mls of absolute alcohol. The solution was acidified with alcoholic hydrochloric acid to pH 4 after which ether was added and a crystalline substance precipitated. This was sucked off and dried, after cooling. Melting point 90.5°–92.5°C.

The following compounds were obtained in an analogous manner according to:
method A: compound of formula II + compound of formula III
or
method B: compound of formula IV + compound of formula V.

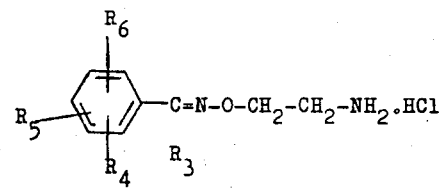

| $R_3$ | $R_4$ | $R_5$ | $R_6$ | Meltpoint °C | method | sedative | anti-convulsive | anti-depressive |
|---|---|---|---|---|---|---|---|---|
|  | 2.OCH$_3$ |  |  | 110,5–111 | A | – | + | + |
|  | 2.OC$_4$H$_9$ |  |  | 70 | B | + | + | – |
|  | 3,4—O—CH$_2$O |  |  | 187–188 | A | – | – | + |
| CH$_3$ | 4.CH$_3$ |  |  | 183–185 | vb1 |  |  | + |
| CH$_3$ | 2.CH$_3$ | 4 CH$_3$ |  | 137–140 | A | – | – | + |
| CH$_3$ | 3,4—CH$_2$—CH$_2$—CH$_2$ |  |  | 193–195 | B | – | + | + |

-continued

| $R_3$ | $R_4$ | $R_5$ | $R_6$ | Meltpoint °C | method | sedative | anti-convulsive | anti-depressive |
|---|---|---|---|---|---|---|---|---|
| $CH_3$ | 3,4—O—$CH_2$—$CH_2$—O | | | 203–206 | vb2 | − | + | + |
| $CH_3$ | 4$SCH_3$ | | | 215–219 | vb5 | | + | + |
| $CH_3$ | 3Cl | 4 $OCH_3$ | 5Cl | 158–159 | A | − | + | + |
| $CH_3$ | 3,4-pyridino-2,3 | | | 235–237 | B | − | | + |
| $CH_3$ | 3,4-indeno-2,3 | | | 257–265 | B | | + | |
| $CH_3$ | 2,3-benzo | 4$OCH_3$ | | 174–175 | A | | + | + |
| $CH_3$ | 3,4-benzoxthiino-2,3 | | | 190–195 | B | | | + |
| $C_2H_5$ | 3$CH_3$ | | | 157–159 | B | | | + |
| $C_2H_5$ | 4$CH_3$ | | | 124,5–125,5 | vb4 | − | − | + |
| $nC_3H_7$ | 4$CH_3$ | | | 82–83 | B | | | + |
| $nC_3H_7$ | 2,3 benzo | 4$OCH_3$ | | 148–149,5 | A | − | + | + |
| $nC_5H_{11}$ | 3$CH_3$ | | | kpt.base 118/0,03 | 116-B | | | |
| $nC_5H_{11}$ | 4$CH_3$ | | | 97–98 | vb3 | − | + | + |
| $nC_5H_{11}$ | 3$CH_3$ | 4$CH_3$ | | 86,5–88 | B | | | + |
| $nC_5H_{11}$ | 3,4—O—$CH_2$—O | | | 105 | A | − | − | + |
| $nC_5H_{11}$ | 4—$SCH_3$ | | | 131,5–133 | A | + | − | + |
| $nC_5H_{11}$ | 2OH | | | 94–96 | B | | | + |
| $nC_5H_{11}$ | 4OH | | | 80–84 maleate | B | | | + |
| $nC_5H_{11}$ | 4$CF_3$ | | | 96–100 | A | + | − | + |
| $nC_5H_{11}$ | 2Cl | 4$CH_3$ | | oil, base | B | | | + |
| $nC_5H_{11}$ | 3Cl | 4$CH_3$ | | 50 | B | | | + |
| $nC_5H_{11}$ | 3Cl | 4OH | | 142–143 base | B | | | + |
| $nC_5H_{11}$ | 2$CH_3$ | 4Cl | 5$CH_3$ | 122–123 | B | | | + |
| $nC_5H_{11}$ | 2$NH_2$ | | | oil base | B | | | + |
| $nC_5H_{11}$ | 4$NH_2$ | | | oil base | B | − | | + |
| $nC_5H_{11}$ | 3$NH_2$ | 4$CH_3$ | | kpt 136-8/0,05 base | B | | | + |
| $nC_5H_{11}$ | 4CN | | | kpt 124-8/0,01 base | B | | | + |
| $CH_2C_6H_5$ | | | | 176–176.5 | A | − | + | + |
| $CH_2$—S—$C_3H_7$ | | | | 100–101 | A | − | − | + |
| $CH_2$—SO—$C_3H_7$ | | | | 144–146 | B | | | + |
| $CH_3$ | | | | 173–175 | vb 6 | − | + | + |
| $CH_3$ | 2,3-benzo | | | 236–238 | vb7 | | | + |
| $i.C_3H_7$ | | | | 90,5–92,5 | vb8 | − | − | + |
| H | H | H | H | 142–124 | A | − | + | + |
| | 2$CH_3$ | | | 142,5–144,5 | A | − | + | + |
| | 2$nC_4H_9$ | | | 93,5–95 | B | + | + | − |
| | 3$OCH_3$ | | | 129–130 | A | − | + | + |
| | 4$OCH_3$ | | | 159–160 | A | − | + | + |
| | 4$OCH_2C_6H_5$ | | | 213–214 | A | | | + |
| | 2Cl | | | 128–129,5 | A | + | − | + |
| | 4Cl | | | 193–195 | A | − | + | + |
| | 2Cl | 4Cl | | 179–181 | A | − | + | + |
| | 2Cl | 6Cl | | 120 | A | − | + | + |
| | 2Br | | | 135,5–136,5 | A | − | + | + |
| | 4N$(CH_3)_2$ | | | 186,5–187 | A | + | + | + |
| $CH_3$ | 4$OCH_3$ | | | 189–191 | A | − | − | + |
| $CH_3$ | 3$OCH_3$ | 4$OCH_3$ | | 212–214 | A | + | − | + |
| $CH_3$ | 2$CH_3$ | 4$OCH_3$ | | 157–158 | A | − | + | + |
| $CH_3$ | 4Cl | | | 192–194 | B | | | + |
| $CH_3$ | 3,4-benzo | | | 237–240 | A | + | + | + |
| $C_2H_5$ | | | | 152–154 | A | − | − | + |
| $C_2H_5$ | 2$CH_3$ | | | 62–64 | B | | | + |
| $C_2H_5$ | 4$OCH_3$ | | | 152–153 | A | + | − | + |
| $C_2H_5$ | 4$OC_2H_5$ | | | 145–146 | A | − | − | + |
| $C_2H_5$ | 4$OnC_4H_9$ | | | 158,5–159,5 | A | − | + | + |
| $C_2H_5$ | 4Cl | | | 150–151 | A | − | − | + |
| $C_2H_5$ | 2Cl | 4$OCH_3$ | | 130–131 | A | − | + | + |
| $C_2H_5$ | 3F | 4$OCH_3$ | | 180 | A | − | − | + |
| $C_2H_5$ | 3$NO_2$ | | | 188–189 | A | − | − | + |
| $C_2H_5$ | 2$NO_2$ | 4$OCH_3$ | | 197–198 | A | − | − | + |
| $nC_3H_7$ | | | | 94,5–95,5 | A | − | − | + |
| $nC_3H_7$ | 4Cl | | | 82–84 | B | | | + |
| $C_3H_5$ | 4F | | | 95,5–97,5 maleate | A | − | − | + |
| $nC_4H_9$ | | | | 82,5–84 | A | − | + | + |
| $nC_4H_9$ | 2Cl | | | 127– 132/0,15 kpt base | B | | | + |
| $nC_4H_9$ | 4Cl | | | 96–98 | B | | | + |
| $nC_4H_9$ | 2,3-benzo | | | oil, base | B | | | + |
| $nC_5H_{11}$ | | | | 93,5–94 | A | − | + | + |
| $nC_5H_{11}$ | 2$CH_3$ | | | 150/0,07 kpt base | B | − | − | + |
| $nC_5H_{11}$ | 3$OCH_3$ | | | 79–80 | B | | | + |
| $nC_5H_{11}$ | 2Cl | | | oil, base | A | − | − | + |
| $nC_5H_{11}$ | 3Cl | | | 98,5–99,5 maleate | A | − | − | + |
| $nC_5H_{11}$ | 4Cl | | | 88–90 | A | + | − | + |
| $nC_5H_{11}$ | 2Cl | 4Cl | | oil, base | A | + | − | + |
| $nC_5H_{11}$ | 3Cl | 4Cl | | 82–86 | A | − | − | + |
| $nC_5H_{11}$ | 2F | | | oil, base | B | | | + |
| $nC_5H_{11}$ | 4F | | | 71–73 | A | − | − | + |
| $nC_5H_{11}$ | 4Br | | | 96–99 | A | − | − | + |
| $nC_5H_{11}$ | 2$CH_3$ | 4Cl | | 75–76,5 | B | | | + |
| $nC_5H_{11}$ | 3Cl | 4$OCH_3$ | | 106–108,5 | B | | | + |
| $nC_5H_{11}$ | 3$NO_2$ | | | oil, base | A | − | + | + |

| R$_3$ | R$_4$ | R$_5$ | R$_6$ | Meltpoint °C | method | sedative | anti-convulsive | anti-depressive |
|---|---|---|---|---|---|---|---|---|
| nC$_5$H$_{11}$ | 3,4-benzo | | | 80–81 | B | | | + |
| nC$_5$H$_{11}$ | 2,3-benzo | | | oil, base | A | + | – | + |
| 3-methyl butyl | | | | 127–128,5 maleate | A | – | – | + |
| nC$_6$H$_{13}$ | | | | 115–116 maleate | A | – | + | + |
| cyclo hexyl | | | | 139,5–142 | B | | | + |
| nC$_7$H$_{15}$ | | | | 112,5–114 maleate | A | + | + | + |
| CH$_2$OC$_3$H$_7$ | | | | 90–91 maleate | A | – | | + |

If nothing is stated in the columns R$_3$, R$_4$, R$_5$, R$_6$, the substituent in question is a hydrogen atom.
+ active
– not active or substantially not active.

TABLET 50 mgms O-(2-amino-ethyl)4'-methoxy-1'-butyronaphthone oxim HCl
335 mgms lactose
60 mgms of potatoe starch
25 mgms talcum
5 mgms magnesium stearate
5 mgms gelatin

SUPPOSITORY 50 mgms O-(2-amino-ethyl)-3'-chloro-4'-hydroxyhexanophenone oxim HCl.
1500 mgms of suppository mass

Injection liquid 25 gms O-(2-amino-ethyl)4'-methylacetophenone oxim HCl
1.80 gms methyl-p.hydroxybenzoate
0.20 gms propyl-p.hydroxybenzoate
9.0 gms of sodium chloride
4.0 gms polysorbate 80 U.S.P. water to 1000 mls.

What is claimed is:

1. The method of combatting depression in a mammal exhibiting depressive symptoms comprising administering to said mammal an antidepressively effective quantity of an antidepressive composition suitable for administration to mammals comprising an antidepressive amount of a compound of the formula

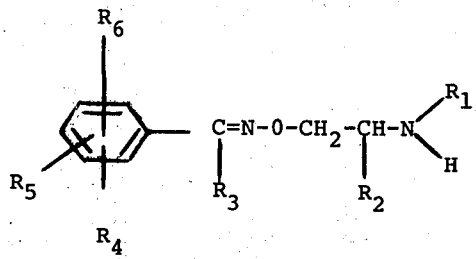

or salts thereof with pharmaceutically acceptable acids wherein R$_1$ is a moiety selected from the group consisting of hydrogen and methyl, R$_2$ is a moiety selected from the group consisting of hydrogen and methyl, R$_3$ is a moiety selected from the group consisting of hydrogen, alkyl, alkoxyalkyl alkylthioalkyl, alkylsulphoxyalkyl each of up to eight carbon atoms and benzoyl, R$_4$ and R$_5$ are each moieties selected from the group consisting of hydrogen, alkoxy of up to six carbon atoms, alkyl of up to six carbon atoms and halogen and R$_6$ is a moiety selected from the group consisting of trifluoromethyl and halogen with the proviso that at least one of R$_1$, R$_2$ and R$_3$ is other than hydrogen when two of R$_4$, R$_5$ and R$_6$ are orthochloro.

2. The method of claim 1 wherein from 10 to 500 mg of the compound is administered to the mammal daily.

3. The method of claim 1 wherein from 10 to 150 mg of the compound is administered to the mammal daily.

4. The method of claim 1 wherein the compound is O-(2-amino-ethyl)-4'(trifluoro-methyl)-hexanophenone oxime.

* * * * *

UNITED STATES PATENT AND TRADEMARK OFFICE
CERTIFICATE OF CORRECTION

PATENT NO. : 3,937,841
DATED : February 10, 1976
INVENTOR(S) : JAN VAN DIJK ET AL It is certified that error appears in the above-identified patent and that said Letters Patent are hereby corrected as shown below:

In the Title Page, add:

-- [30] Foreign Applications Priority Data
April 5, 1967 Netherlands 6,704,810
December 14, 1967 Netherlands 6,717,001 --.

[62] after "Aug. 11, 1972" insert -- Said Application Ser. No. 279,971 being a division of Application Ser. No. 715,571, filed March 25, 1968 and now United States Patent 3,692,835 --.

Signed and Sealed this

Fourteenth Day of September 1976

[SEAL]

Attest:

RUTH C. MASON
Attesting Officer

C. MARSHALL DANN
Commissioner of Patents and Trademarks